United States Patent [19]

DePaola

[11] 4,078,053
[45] Mar. 7, 1978

[54] HIGH-CONCENTRATION FLUORIDE PREPARATIONS AND USE FOR PREVENTING CARIES

[75] Inventor: Paul F. DePaola, Lexington, Mass.

[73] Assignee: Forsyth Dental Infirmary for Children, Boston, Mass.

[21] Appl. No.: 659,833

[22] Filed: Feb. 20, 1976

[51] Int. Cl.$^2$ .............................................. A61K 7/18
[52] U.S. Cl. ...................................................... 424/52
[58] Field of Search .......................................... 424/52

[56] References Cited

PUBLICATIONS

Caslavska et al., Chem. Abstr. 76 #30670e, (1972) of Arch. Oral. Biol. L6(10): 1173–1180, (1971), "Response of Human Enamel to Topical Applicaton of Ammonium Fluoride".

Wei et al., Chem. Abstr. 84 #53898q, Mar. 1, 1976 of J. Dent. RBS. 54(6):1234 (1975), "Relative Effects of Ammonium Fluoride and Acidulated Phosphate Fluoride Solutions on Human Enamel".

DePaola et al., Chem. Abstr. 84 #54283x, Mar. 1, 1976, of U.S. NTIS, PB–24319 OREP., (1975) 38 pp. "Effect on Surface Enamel Fluoride and Dental Caries of Semiannual Topical Applicaton of 0.62 Ammonium Fluoride".

*Primary Examiner*—Shep K. Rose
*Attorney, Agent, or Firm*—Richard P. Crowley

[57] ABSTRACT

High-concentration fluoride containing preparations, particularly ammonium fluoride, in mouth rinses at a concentration of greater than 2000 ppm significantly inhibit caries, particularly by frequent; e.g., daily, use in connection with new, erupting teeth of children.

14 Claims, No Drawings

HIGH-CONCENTRATION FLUORIDE PREPARATIONS AND USE FOR PREVENTING CARIES

REFERENCE

This invention was made in the course of and during the performance of studies and work made under a grant from the U.S. Department of Health, Education and Welfare.

BACKGROUND OF THE INVENTION

Various fluoride compounds have been suggested for use in dentifrice compositions to inhibit caries (see, for example, U.S. Pat. No. 3,029,191 incorporated by reference). The amount of fluoride employed is typically a maximum of about 200 ppm in commerical preparations, with sodium fluoride and stannous fluoride often employed as the source of fluoride ion. Further, the efficacy of daily rinsing with dilute fluoride solutions has been demonstrated in mouth-rinse fluoride solutions. The use of fluoride ion concentration in mouth rinses containing sodium fluoride has varied from about 0.0045% to as high as 0.3%, with the frequency of use ranging from one rinse per day to one rinse per month.

SUMMARY OF THE INVENTION

My invention relates to preparations containing ammonium fluoride for use in preventing or inhibiting caries, particularly in newly erupting teeth. In particular, my invention concerns preparations, such as a mouth-rinse solution and paste and gel dentifrices, containing high concentrations of ammonium fluoride. More particularly, my invention is directed to the high-frequency use of preparations containing high concentrations of 1000 ppm or over of ammonium fluoride.

I have found that high concentrations of ammonium fluoride preparations are particularly and unexpectedly effective in the inhibition of caries, particularly newly erupting teeth in children, and with frequent daily or greater use of the preparations. Surprisingly, I have discovered that the use of ammonium fluoride provides a greater reduction in caries than sodium fluoride at the same fluoride-ion concentration level in comparative in vivo tests, and that ammonium fluoride has a greater effect on caries reduction on newly erupted teeth.

My invention provides for the preparation and use of compositions for use in the oral cavity, particularly of children under the age of about 12, such as in the form of powder, paste or gel dentifrices, and particularly mouth-rinse solutions, with a concentration of ammonium fluoride over about 500 ppm, particularly over 800 ppm, and preferably about 800 to as high as 3000 ppm; e.g., 800 to 2000 ppm.

The active ingredient of ammonium fluoride may be incorporated into liquids, creams, gels, pastes, solutions, chewing gum, dental floss, lozenges, powders or other suitable vehicles. The ammonium fluoride may be employed alone or in combination with other fluorides, such as sodium or stannous fluoride, and with other compounding ingredients commonly employed in such dental preparations, to include, but not be limited to: polishing agents like calcium phosphate; humectants and binders such as glycerin or sorbitol; gelling agents such as gum-like materials like sodium carboxymethyl cellulose, starch, etc.; and adjunct materials like surfactants, preservatives, sweetening agents like saccharin, dyes, flavoring agents, buffers, thickeners, emulsifiers, bacteriocides and the like as set forth, for example, in U.S. Pat. No. 3,029,191.

Particularly, the preferred preparation of my invention is ammonium fluoride containing aqueous-bond mouth-rinse solutions which are employed on a basis of at least four to five separate days each week; e.g., once or twice daily by the user, and which contain 800 to 1200 ppm of ammonium fluoride.

DESCRIPTION OF THE EMBODIMENTS

A mouth-rinse solution of the invention would comprise water, ammonium fluoride in an amount to obtain the desired concentration (0.008 to 0.03%), a sweetening agent, anhydroxy compound like glycerin or sorbitol; e.g., 0.005 to 0.1%, a dye, a surfactant (0.001 to 0.1%) and a flavoring agent. The amount of the rinse solution to be employed depends on the ammonium fluoride ion concentration, but should be from about 1 to 10 ml daily for children under about 12 years of age; e.g., about 5 ml for children 8 to 12 years old, which dose levels permit use without damage or fluorosis.

A double-blind clinical trial was conducted in a non-fluoridated community to determine the effects of enamel F and caries experience of daily rinsing in school with 1000 ppm solutions of $NH_4F$ or $NaF$ at pH 4.4. The subjects were 10 to 12-year old children ($n \simeq 200$/group at baseline), about one-half of whom reported the usage of F supplements. Dental caries (DFS index) and enamel F (in vivo biopsy technique) were evaluated at baseline, 12 months and 24 months. Enamel F values were statistically adjusted to a standardized depth. Supplement users had a conspicuously higher enamel F and lower DFS at the outset, as well as generally lower caries increments over the study. In year one, the overall caries reductions (supplement users and nonusers combined) were 23% ($NH_4F$) and 33% (NaF), $p<0.01$. For year two, the treatment effects were apparently greater: a 54% DFS reduction in $NH_4F$ subjects and 47% for those using NaF, $p<0.01$. Benefits were noteworthy in teeth erupting during the 24 months of the study, with significant ($p<0.01$) DFS reductions of 69% ($NH_4F$) and 48% (NaF). Enamel F levels at the end of two years were 3124 ppm ($NH_4F$), 2777 ppm (NaF) and 2627 ppm (Placebo), $p=0.025^4$. My findings indicate that daily high-concentration ammonium fluoride rinses or other preparations have considerable caries-inhibiting effects. In teeth present at baseline, treatment effects were similar for the two agents, and similar for supplement users and non-users. In newly erupting teeth, however, the data establishes the greater effect from $NH_4F$, and more relative benefit to nonusers of supplements.

Prior to the initiation of the clinical trial, extensive toxicological studies of the proposed test agents were conducted in animals, and the proper clearances were obtained from the Food and Drug Administration. A flavoring was developed for the rinse solutions and arrangements were made to provide the rinses properly bottled, coded and shipped during the course of the investigation. Norwood, Massachusetts, a non-fluoridated, middle-class community sixteen miles southwest of Boston, was selected as the test locale. Consent forms were distributed to approximately 750 fifth and sixth-grade students, essentially 10 to 12 years old, from five elementary schools. On the basis of the returns, it was possible to incorporate 614 children into the study. Unexectedly, nearly one-half of the participants responded "Yes" to one or the other of the following questions which were included on the consent forms: (1) "Has your child ever taken fluoride pills or drops?"; (2) "Has your family ever lived in a community which had a naturally or artificially fluoridated water supply?". A very large majority of the total number of "yeses" was in response to question (1) dealing with F supplements. The original intent had been to exclude children reporting any history of exposure to systemic fluorides, since it was expected that they would constitute a small minority. It was now apparent, however, that this would render the sample sizes inadequate. It was decided, therefore, to retain such subjects and to conduct subsequent data analyses on the basis of: (1) all subjects combined; and (2) subjects distinguished as to history of systemic fluorides. Hereafter, subjects who reported a prior history of exposure to systemic F are referred to as "exposed", while those with a negative history are termed "nonexposed". Clinical procedures were carried out in the schools utilizing portable equipment. Subjects received a light dental prophylaxis, an enamel biopsy on a randomly selected upper central incisor, a dental examination (clinical plus bitewing radiographic), and were randomly assigned to treatment groups. The caries findings were recorded on optical-scanning sheets for computer analysis. Diagnostic criteria have been described previously. The biopsy samples were analyzed chemically and the data were treated statistically so as to compensate for the problem of variable sampling depth. When all subjects in a given school were completed, daily rinsing was initiated and the portable equipment moved to the next school. Rinses were supervised by the school nurses during the first year and by the nurses and teachers the second year. Close contact was maintained with the rinse supervisors by members of the investigative team throughout the study to be sure that treatments were carried out properly. The formulations of the experimental solutions were as follows:

| 1. The ammonium fluoride rinse | | |
|---|---|---|
| Component | Amount | Typical Range |
| Distilled H$_2$O | 1000 ml | |
| NH$_4$F | 1.95 g | 1.0 to 6.0 g |
| H$_3$PO$_4$-buffer | 175 mg | 100 to 300 mg |
| Na saccharin sweetener | 800 mg | 400 to 1200 mg |
| K sorbate-preservative | 1020 mg | 500 to 2000 mg |
| Dye-W.F. grape shade 91% | 10 mg | 1 to 25 mg |
| Tween 20-miscible surfactant | 440 mg | 200 to 2000 mg |
| Grape flavor P8599-flavoring agent | 450 mg | 100 to 2000 mg |
| Vanilla F 59-137-T-flavoring agent | 60 mg | 100 to 2000 mg |
| 2. The sodium fluoride rinse | | |
| Component | Amount | |
| Distilled H$_2$O | 1000 ml | |
| NaF | 2.21 g | |
| H$_3$PO$_4$ | 175 mg | |
| Na saccharin | 600 mg | |
| Potassium sorbate | 1020 mg | |
| Dye-W.F. grape shade 91% | 10 mg | |
| Tween 20 | 440 mg | |
| Grape flavor P 8599 | 450 mg | |
| Vanilla F 59-137-T | 60 mg | |

The placebo agent contained no fluoride and was flavored and colored so as to be as similar to the test solutions as possible. Rinses were carried out daily in school over a period of two full school years. The solutions were distributed to the children in color-coded cups by the supervisor who had a list indicating the appropriate agent for each subject. The children rinsed for exactly one minute (determined by a mechanical timer) and expectorated into the cup. A daily record was kept of absentee subjects.

Subjects were reexamined clinically and by radiograph at 12 and 24 months, without reference to previous findings. At the 12 month follow-up, a random one-half of the subjects were rebiopsied, utilizing the upper central incisor opposite to the one used at baseline. At 24 months, the other one-half were rebiopsied again on the upper central incisor not previously sampled.

All caries findings reported herein pertain to subjects who participated throughout the investigation. Subject losses amounted to about 10% per year, per group, and were generally attributable to factors unrelated to the study. No significant differences in age or past caries were observed between treatment groups, either for the exposed subjects or the nonexposed.

The mean number of rinses for continuous participants in each group over the course of the study were 285.17 (NH$_4$F), 267.76 (NaF) and 288.90 (placebo), with no significant differences between groups. In the first 12 months, there were overall caries reductions of 23% for the NH$_4$F subjects and 33% for those using NaF. The caries activity of the second 12 months is shown in Table I.

Table I

OVERALL CARIES INCREMENTS (DF SURFACES) DURING THE SECOND TWELVE MONTHS IN SUBJECTS CATEGORIZED BY TREATMENT GROUP AND PRIOR EXPOSURE TO SYSTEMIC F

| | Prior Exposure to Systemic F | | | | | |
|---|---|---|---|---|---|---|
| | No | | Yes | | All subjects | |
| Group | N | Mean | N | Mean | N | Mean |
| NH$_4$F | 85 | 2.65 (3.04)* | 74 | 1.60 (2.31) | 159 | 2.16 |
| NaF | 92 | 2.70 (2.75) | 66 | 2.17 (2.35) | 158 | 2.48 |
| Placebo | 81 | 5.52 (5.27) | 77 | 3.75 (4.64) | 158 | 4.66 |
| F ratio | | 15.36 | | 8.36 | | |
| Probability | | <.01 | | <.01 | | |

*Figures in parentheses are standard deviations

The overall reductions were 54% (NH$_4$F) and 47% (NaF). The differences were highly significant for both exposed and non-exposed subjects, although the F ratio was considerably higher in the case of the unexposed. The influence of systemic F was again observed in the controls with a 32% lesser caries experience (3.75 vs. 5.52) for subjects with a positive history.

Table II combines the data of both study years, and shows the cumulative caries experience of the different groups over the entire study. Children rising with the NH$_4$F agent experienced a significant and unexpected caries reduction over the 24 months of 44%.

Table II

OVERALL CARIES INCREMENTS (DF SURFACES) DURING THE TWENTY-FOUR MONTHS OF THE STUDY IN SUBJECTS CATEGORIZED BY TREATMENT GROUP AND PRIOR EXPOSURE TO SYSTEMIC F

| | Prior Exposure to Systemic F | | | | | |
|---|---|---|---|---|---|---|
| | No | | Yes | | All subjects | |
| Group | N | Mean | N | Mean | N | Mean |
| NH$_4$F | 85 | 4.82 (4.69)* | 74 | 2.88 (3.34) | 159 | 3.92 |
| NaF | 92 | 4.60 (4.25) | 66 | 3.30 (3.08) | 158 | 4.06 |
| Placebo | 81 | 8.61 | 77 | 5.38 | 158 | 7.04 |

Table II-continued
OVERALL CARIES INCREMENTS (DF SURFACES) DURING THE TWENTY-FOUR MONTHS OF THE STUDY IN SUBJECTS CATEGORIZED BY TREATMENT GROUP AND PRIOR EXPOSURE TO SYSTEMIC F

|  | Prior Exposure to Systemic F | | | | |
|---|---|---|---|---|---|
|  | No | | Yes | | All subjects |
| Group | N | Mean | N | Mean | N Mean |
|  |  | (7.65) |  | (7.24) |  |
| F ratio |  | 13.05 |  | 5.24 |  |
| Probability |  | <.01 |  | <.01 |  |

*Figures in parentheses are standard deviations

Over the course of the investigation, control subjects with a prior history of systemic F had a DF surface increment of 5.38 vs. 8.61 for those with a negative history, a difference of 38%. There were no significant differences in mean numbers of teeth erupting between the study groups or the subgroups. The caries activity in newly erupted teeth over 24 months is summarized in Table III.

Table III
DF SURFACE INCREMENT IN TEETH ERUPTING DURING THE 24 MONTHS OF THE STUDY FOR SUBJECTS CATEGORIZED BY TREATMENT GROUP AND PRIOR EXPOSURE TO SYSTEMIC F

|  | Prior exposure to systemic F | | | | | |
|---|---|---|---|---|---|---|
|  | No | | Yes | | All subjects | |
| Group | N | Mean | N | Mean | N | Mean |
| $NH_4F$ | 85 | 0.40 | 74 | 0.55 | 159 | 0.47 |
|  |  | (0.79)* |  | (0.93) |  |  |
| NaF | 92 | 0.83 | 66 | 0.76 | 158 | 0.80 |
|  |  | (1.34) |  | (1.28) |  |  |
| Placebo | 81 | 1.82 | 77 | 1.26 | 158 | 1.55 |
|  |  | (2.25) |  | (2.09) |  |  |
| F ratio |  | 17.76 |  | 4.18 |  |  |
| Probability |  | <.01 |  | .01<p<.05 |  |  |

*Figures in parentheses are standard deviations

The data show that the ammonium fluoride solution unexpectedly inhibited dental caries by 70%, and the sodium fluoride only by 48%. The caries experience of the two treated groups was significantly different from that of the controls, and significantly different from one another. The effects were conspicuous both in exposed subjects, with reductions of 56% ($NH_4F$) and 40% (NaF), and in the nonexposed, with differences of 78% ($NH_4F$) and 54% (NaF). Again, however, the effects reached a higher level of significance in the latter.

The enamel biopsy data show that the adjusted enamel F values at the baseline examination for subjects categorized by group and prior exposure to systemic F appeared to be well-balanced with respect to enamel F at the outset. Table IV contains the baseline F levels for subjects who were rebiopsied at 12 months, and shows that the initial enamel F of the $NH_4F$ subjects was anomalously low (p=0.014), precluding a meaningful comparison of F concentrations between treatment groups at the end of the first year.

Table IV
ADJUSTED ENAMEL F VALUES (IN PPM) AT THE BASELINE EXAMINATION FOR SUBJECTS WHO WERE BIOPSIED AT 12 MONTHS

|  | Prior exposure to systemic F | | | | | |
|---|---|---|---|---|---|---|
|  | Yes | | No | | All | |
| Group | N | Mean | N | Mean | N | Mean |
| $NH_4F$ | 24 | 2652 | 30 | 1993 | 54 | 2286 |
|  |  | (772)* |  | (554) |  | (732) |
| NaF | 31 | 3017 | 34 | 2385 | 65 | 2686 |
|  |  | (888) |  | (680) |  | (842) |
| Placebo | 34 | 2862 | 24 | (2442) | 58 | 2688 |
|  |  | (858) |  | (636) |  | (795) |
| All | 89 | 2859 | 88 | 2267 | 177 | 2565 |

Table IV-continued
ADJUSTED ENAMEL F VALUES (IN PPM) AT THE BASELINE EXAMINATION FOR SUBJECTS WHO WERE BIOPSIED AT 12 MONTHS

|  | Prior exposure to systemic F | | | | | |
|---|---|---|---|---|---|---|
|  | Yes | | No | | All | |
| Group | N | Mean | N | Mean | N | Mean |
|  |  | (849) |  | (651) |  | (811) |

*Figures in parentheses are standard deviations
Anova Summary

| Source | F-test | Significance |
|---|---|---|
| Treatments | 4.405* | 0.014 |
| Systemic F | 25.350*** | <0.001 |
| Treatment and systemic F | 0.446 | >0.500 |

Tables V and VI give the findings for subjects biopsied at the beginning and at the end of the study. There were no important group differences in group F levels at the outlet (Table V), but by the end of 24 months (Table VI), significant changes had occurred. The final F determinations were 3124 ppm ($NH_4F$), 2771 ppm (NaF) and 2603 ppm (placebo). The trend toward increased F levels for treated subjects (which was significant in the prevalence data of Table VI) is apparent. There was a significantly greater uptake of fluoride in nonexposed children which was due partly to a spurious F elevation in nonexposed controls, but it is also apparent that the nonexposed children in each treated group acquired more F than the comparable exposed children.

Table V
ADJUSTED ENAMEL F VALUES (IN PPM) AT THE BASELINE EXAMINATION FOR SUBJECTS WHO WERE BIOPSIED AT 24 MONTHS

|  | Prior exposure to systemic F | | | | | |
|---|---|---|---|---|---|---|
|  | Yes | | No | | All | |
| Group | N | Mean | N | Mean | N | Mean |
| $NH_4F$ | 35 | 2812 | 36 | 2063 | 71 | 2432 |
|  |  | (611)* |  | (503) |  | (671) |
| NaF | 29 | 2553 | 34 | 2131 | 63 | 2325 |
|  |  | (803) |  | (813) |  | (830) |
| Placebo | 31 | 2882 | 39 | 1982 | 70 | 2381 |
|  |  | (934) |  | (530) |  | (858) |
| All | 95 | 2756 | 109 | 2055 | 204 | 2381 |
|  |  | (790) |  | (622) |  | (786) |

*Figures in parentheses are standard deviations
Anova Summary

| Source | F-test | Significance |
|---|---|---|
| Treatments | 0.388 | >0.500 |
| Systemic F | 48.476*** | <0.001 |
| Treatment and systemic F | 2.025 | 0.135 |

Table VI
ADJUSTED ENAMEL F VALUES (IN PPM AT TWENTY-FOUR MONTHS FOR SUBJECTS CATEGORIZED BY GROUP AND PRIOR EXPOSURE TO SYSTEMIC F

|  | Prior exposure to systemic F | | | | | |
|---|---|---|---|---|---|---|
|  | Yes | | No | | All | |
| Group | N | Mean | N | Mean | N | Mean |
| $NH_4F$ | 35 | 3249 | 35 | 2999 | 70 | 3124 |
|  |  | (1206)* |  | (888) |  | (1059) |
| NaF | 28 | 2868 | 32 | 2687 | 60 | 2771 |
|  |  | (769) |  | (1249) |  | (1048) |
| Placebo | 30 | 2880 | 36 | 2373 | 66 | 2603 |
|  |  | (1249) |  | (841) |  | (1068) |
| All | 93 | 3015 | 103 | 2683 | 196 | 2841 |
|  |  | (1104) |  | (1019) |  | (1072) |

*Figures in parentheses are standard deviations
Anova Summary

| Source | F-test | Significance |
|---|---|---|
| Treatments | 3.796* | 0.025 |
| Systemic F | 4.284* | 0.040 |
| Treatment and systemic F | 0.433 | >0.500 |

The data show clearly a greater deposition of F from the NH$_4$F agent than from the NaF. The biopsy data also permit a comparison of subjects reporting exposure to systemic F vs. those without exposure. The data showed a highly significant difference in enamel F for the two groups at the outset of the study. The same pattern was evident 24 months later (Table VI). The placebo values for exposed and nonexposed children at the end of the trial were similar to the overall values for the exposed and nonexposed at baseline. On the other hand, the treated values, by the end of 24 months, had increased, although the exposed subjects continued to have a relatively higher F level.

It was found throughout the investigation that exposed children were characterized by a higher enamel F content. Thus, the reasonable expectations were fulfilled in that exposed subjects had consistently higher enamel fluoride and lower dental caries. At the outset, it would have been difficult to predict the magnitude of the expected difference in caries prevalence and incidence between the exposed and nonexposed children, since the only thing known about the exposed subjects was that, at some time in their lives, they had taken F supplements (or in a few instances F water). In general, the caries and biopsy findings in exposed vs. nonexposed subjects conform closely to anticipated patterns which considerably enhance the credibility of the test results.

At the end of the first year, overall caries reductions of 23 to 33% were apparent in the treatment groups. The amonium fluoride agent did not perform more effectively than the sodium fluoride, and the protection imparted by the high F concentrations (1000 ppm) of the rinses did not appear any greater than that observed at the end of one year in recent studies involving much weaker (200 ppm) agents. The pattern of the second 12 months, however, indicated a marked increase in treatment effect. Subjects using ammonium fluoride enjoyed a 54% reduction in DF surface increment, while the corresponding reductions for those using sodium fluoride were 47%.

The analyses based upon teeth erupting during the course of the study are of particlar interest. The ammonium F reduced caries in new teeth by 70%, while for the sodium F the reduction was 48%. In this instance, the effects of the two agents were significantly and unexpectedly different ($p < 0.013$). In the more responsive erupting teeth, the data indicates a definite cation effect, presumably having to do with the increased fluoride deposition by common fluoride. Thus, increased fluoride led to an unexpected differential effect in the newly erupted teeth. It is believed that an increased capacity for the deposition of F along with a heightened responsiveness of new teeth to this action is a possible explanation for the more pronounced caries-inhibiting effect of the NH$_4$F agent in the erupting teeth.

All subjects with a suitable surface were biopsied at the start of the study, and the data indicate that the experimental groups were well-balanced with respect to enamel F. At 12 and 24 months, random subsamples within each of the study groups were biopsied using the upper central incisor homologous to the one used at baseline. An analysis of the baseline F levels of the subsamples rebiopsied at 12 months revealed that the initial enamel F concentration of the NH$_4$F subjects was anomalously low (2286 ppm) compared to the NaF (2686 ppm) and placebo children (2688 ppm). The F value for treatment groups was 4.405, $p < 0.014$. This was an unfortunate chance effect, associated with the random selection of the 12-month biopsy subjects, and it precluded a meaningful evaluation of F levels at the 12-month mark. Such was not the case, however, at 24 months. The subgroups assayed at the end of the study were well-balanced with respect to initial enamel fluoride (F value for treatment groups = 0.388, $p > 0.500$). Therefore, an analysis of group F levels at 24 months was carried out and revealed significant differences. The subgroup of children who had been using the ammonium F rinse showed a fluoride value of 3124 ppm vs. 2771 ppm for the sodium fluoride subjects, and 2603 ppm for those in the placebo group.

The different F increments by group represent real treatment effects. The observed changes in fluoride were 665 ppm in the NH$_4$F group, 367 ppm in the NaF group and 236 ppm for the controls. The pattern of F deposition was paralleled by the caries inhibition in newly erupting teeth, but not in the older teeth which appear to have benefited equally from each test agent.

Subjects who were fluoride-deficient at the outlet of the study enjoyed relatively greater F uptake and caries suppression as a result of rinsing than those whose fluoride levels were high to begin with. In the study as a whole, caries reductions were conspicuous in both exposed and nonexposed children, but were stronger statistically speaking for the latter. In newly erupting teeth, there appears to be a trend indicating more benefit to nonexposed children. It is important to note that rinsing with the test agents may be worthwhile even for children taken F supplements or drinking fluoridated water.

The use of high-potency rinses on a frequent basis in the present study prompts comparison to: (1) previous studies utilizing frequent low-concentration agents; and (2) previous studies involving the less frequent (e.g., 1/week, 2/month) use of high concentrations. In the category of the former, one recent study offers a particularly good basis for comparison. It was conducted by some of the same investigators as the present effort (although not the same examiner), took place in the same community, involved children of similar ages (about 1 year younger on the average), and the overall caries experience for the controls in the first two years was comparable to that reported herein. The test agents were a neutral and an acidulated 200 ppm F rinse used daily in school, although there proved to be no significant difference in the performance of the two solutions. The findings, compared to those of the present study, were as follows:

| Percentage reduction in DF Surfaces | All teeth | | Erupting teeth | |
|---|---|---|---|---|
| | earlier study (200 ppm F) | my study (1000 ppm F) | earlier study (200 ppm F) | my study (1000 ppm F) |
| During year one | 16 | 23 – 33 | | |
| During year two | 29 | 47 – 54 | | |
| Over two years | 25 | 42 – 44 | 35 | 48 – 70 |

In these two similar investigations, the high-potency rinses have provided the greater benefit, especially during the second year, and especially in erupting teeth. I have found that the frequent rinses (e.g., every day or every school day) are more effective in a high concentration, such as 1000 ppm F, than in the more usual lower concentration of about 200 ppm. Increased frequency of rinsing yields increased benefit.

Daily rinsing in school with ammonium and sodium fluoride solutions containing 1000 ppm F, and at a pH of 4.4, produced overall caries reductions of 44 and 42%, respectively. The two agents did not differ in effectiveness against total caries experience.

With respect to teeth erupting during the course of the study, the ammonium fluoride agent reduced new DF surfaces by 70% vs. 48% for the sodium fluoride rinse. In this case, the two treatment effects were significantly different (p 0.01). The differential reaction to the treatment agents by the erupting teeth suggests a heightened responsiveness on the part of new teeth to the $NH_4+$ agent, viz. a superior capacity for the deposition of F.

The enamel F levels of the treatment groups were well-balanced at the outset. At the end of the study, however, there were significant intergroup differences, the mean values being 3124 ppm ($NH_4F$), 2771 ppm (NaF) and 2603 ppm (placebo).

A comparison of the present findings to those in other studies suggests that rinses contaning more than 800 ppm; e.g., 1000 ppm F, are superior to those with approximately 200 ppm F when used on school days.

The foregoing use of a mouth-rinse solution has been given for the purposes of illustration of a preparation only, and other preparations may be prepared in accordance with my invention.

Another representative mouth wash of my invention which contains ethanol is:

| | |
|---|---|
| N-lauroyl sarcoside surfactant (alkali metal or $NH_4$ salt) | 0.1 parts |
| Ammonium fluoride | 800 ppm |
| Ethyl alcohol | 10; e.g., 5 to 20 parts |
| Flavoring agent | 0.15 parts |
| Soluble saccharin-sweetener | 0.01 parts |
| Water | Balance to 100 parts |

A representative dental preparation of my invention is:

| | |
|---|---|
| Ammonium N-lauroyl sarcoside surfactant | 2.0 parts (e.g., 0.5 to 4.0) |
| Ammonium fluoride | 2000 ppm |
| Calcium pyrophosphate (or sodium mixture) water-insoluble polishing agent | 50 parts (e.g., 40 to 65) |
| Glycerin-humectant | 30 parts (e.g., 20 to 40) |
| Moss gum-thickener | |
| Sodium carboxymethyl cellulose | 0.8 parts (e.g., 0.1 to 2.0) |
| Saccharin-sweetener | 0.2 (e.g., 0.1 to 0.5) |
| Sodium benzoate-preservative | 0.5 (e.g., 1 to 1.0) |
| Flavor-peppermint | 1.0 (e.g., 0.1 to 3.0) |
| Water | Balance to 100 parts |

Optionally, other ingredients like alumina, silica gel, titanium dioxide, ammonium phosphate, etc. may be used. Other preparations include transparent gel dentifrices and dental powders. Contact of the newly erupted teeth can be accomplished by any means, such as oral application of a solution by swab, rinsing and expectoration of the rinse, brushing with paste, gel or powder, or by chewing, spraying and the like.

What I claim is:

1. A method for the prevention of caries in newly erupted teeth of a subject, which method comprises contacting the newly erupted teeth in the oral cavity daily about four to seven times a week with a composition containing a high concentration of from 500 to 3000 ppm of ammonium fluoride.

2. The method of claim 1 which includes contacting the newly erupted teeth by rinsing the oral cavity with an aqeuous flavored mouth-rinse solution containing about 500 to 1200 ppm of the ammonium fluoride.

3. The method of claim 1 which includes contacting the newly erupted teeth by brushing the teeth with a composition which comprises a gel-like or paste-like mixture containing a water-insoluble polishing agent.

4. The method of claim 1 which includes rinsing the mouth daily with about 1 to 20 ml of an aqueous acidic flavored mouth-rinse solution at a pH of about 4.4 containing about 1000 ppm of ammonium fluoride.

5. The method of claim 1 which includes rinsing the oral cavity containing newly erupted teeth with a mouth-rinse solution which comprises:

| | |
|---|---|
| Distilled water | 1000 ml |
| Ammonium fluoride | 2.0 grams |
| Phosphoric acid | 100 to 600 mg |
| Sodium saccharin | 400 to 1200 mg |
| Preservative | 500 to 2000 mg |
| Dye | 1 to 25 mg |
| Miscible surfactant | 200 to 2000 mg |
| Flavoring agent | 100 to 2000 Mg. |

6. The method of claim 1 wherein the subject is a child of an age of from about 8 to 10 years of age.

7. The method of claim 1 wherein the composition is an acidic mouth-rinse solution.

8. The method of claim 1 wherein the composition comprises a transparent gel-like or a paste-like dentifrice containing a water-insoluble polishing agent.

9. The method of claim 1 wherein such contacting occurs for a period of greater than 1 year.

10. A method for prevention of caries in newly erupted teeth in the oral cavity of children under the age of about 12 years, which method comprises:
rinsing the oral cavity with an aqueous-flavored buffered mouth-rinse solution having as active ingredients from about 800 to 1200 ppm of ammonium fluoride, the rinsing occurring daily at least four times a week for a period of at least 1 year.

11. A mouth-rinse solution for frequent rinsing of an oral cavity of a subject containing newly erupted teeth, which solution comprises an aqueous-flavored buffered solution containing as an active ingredient from about 500 to 3000 ppm of ammonium fluoride.

12. The solution of claim 11 wherein the ammonium fluoride amount is 800 to 1200 ppm.

13. The solution of claim 11 which comprises a phosphate buffer to buffer the solution at a pH of about 4.4.

14. The solution of claim 11 wherein the solution comprises:

| | |
|---|---|
| Distilled water | 1000 ml |
| Ammonium fluoride | 2.0 grams |
| Phosphoric acid | 100 to 600 mg |
| Sodium saccharin | 400 to 1200 mg |
| Preservative | 500 to 2000 mg |
| Dye | 1 to 25 mg |
| Miscible surfactant | 200 to 2000 mg |
| Flavoring agent | 100 to 2000 mg. |

* * * * *